United States Patent [19]
Patel

[11] Patent Number: 5,958,191
[45] Date of Patent: Sep. 28, 1999

[54] COLUMN FOR THE SEPARATION OF A VOLATILE LIQUID FROM A MIXTURE WITH ANOTHER LIQUID OF LOWER VOLATILITY

[75] Inventor: Suru L. Patel, Alberta, Canada

[73] Assignee: Kvaerner Canada, Inc., Alberta, Canada

[21] Appl. No.: 08/927,824

[22] Filed: Sep. 11, 1997

[51] Int. Cl.$^6$ ........................................... B01D 3/32
[52] U.S. Cl. ..................... 202/158; 95/164; 95/263; 96/181; 96/204; 202/153; 203/49; 203/99; 203/DIG. 9
[58] Field of Search ................. 203/41, 49, 18, 203/99, DIG. 23, DIG. 9, DIG. 19; 202/153, 158; 568/916; 196/111; 95/263, 164; 96/181, 204

[56] References Cited

U.S. PATENT DOCUMENTS

| | | | |
|---|---|---|---|
| 3,039,845 | 6/1962 | Steinrotter et al. | 95/190 |
| 4,775,395 | 10/1988 | Rojey et al. | 95/263 |
| 5,339,648 | 8/1994 | Lockett et al. | 202/158 |
| 5,565,066 | 10/1996 | Marker et al. | 203/41 |

FOREIGN PATENT DOCUMENTS

| | | |
|---|---|---|
| 1113684 | 2/1959 | Germany . |
| 3310703 | 12/1988 | Japan . |
| 4349101 | 12/1992 | Japan . |
| 8126830 | 5/1996 | Japan . |

*Primary Examiner*—Virginia Manoharan
*Attorney, Agent, or Firm*—James G. O'Neill

[57] ABSTRACT

A column to regenerate methanol from a methanol-water mixture includes a circular column having two contact beds with a plurality of gas inlets connected thereto to split the entering feed gas so that approximately equal portions are fed through each bed. An inlet near the top of the column allows a methanol-water mixture to be introduced to flow down through the two contact beds, countercurrent to the feed gas.

7 Claims, 2 Drawing Sheets

COLUMN FOR THE SEPARATION OF A VOLATILE LIQUID FROM A MIXTURE WITH ANOTHER LIQUID OF LOWER VOLATILITY

BACKGROUND OF THE INVENTION

1. Field of the Invention

This invention related generally to regeneration of volatile liquids, and more particularly, to an improved column for the separation of a volatile liquid from a mixture with another liquid of lower volatility.

2. Description of Related Art

In systems where a vapor, such as natural gas, nitrogen, steam or some other gas, is used to strip a lower boiling component (solvent) from a mixture with a higher boiling component (e.g., methanol from methanol-water mixture using natural gas), a column is used in which the stripper column diameter is usually dictated by the amount of stripping gas or vapor required to effect the separation. The amount of gas in turn is dependent on its temperature and the carrying capacity for the solvent and the concentration of the solvent in the mixture being fed to the tower.

In presently known systems in which a column is used to strip (regenerate) methanol from a methanol-water mixture, a methanol rich water stream flows down the column, which is packed with a high efficiency structured packing, (such as Sulzer BX), and a warm feed gas stream is fed from the bottom of the column to flow up the column countercurrently. During the passage through the column, the methanol from the rich methanol-water stream is vaporized into the upflowing warm gas stream. The gas stream is usually water saturated and does not pick up water. However, as it is undersaturated or free of methanol, it drives off the methanol into the vapor phase. Typically, between 50 to 60 percent of the total feed gas stream passes through the entire column, for effective regeneration of the rich methanol water stream. The remainder of the feed gas is split and bypasses the column. The amounts to be fed to the column and split are determined or set by the process operating conditions. The diameter of the column is also determined or set by the operating pressure, temperature and flow rate of the gas and liquid streams flowing through it. Usually, the gas stream is the controlling determinate of the column diameter. The depth of the packing is determined or set by the purity of a bottom water specification, with respect to methanol content, and the split of the gas flowing through the column and that which bypasses the column.

German patent number 1113684 describes a process for desorption of a gas-laden wash-liquid wherein foam in systems having a boiling liquid fed to a column for desorption is suppressed. The process applies only to systems where in the first step, the gas and liquid are flowing co-currently. Also, the patent does not show any means of reducing the column diameter, nor does it relate in any way to the present invention.

U.S. Pat. No. 4,775,395 to Rojey et al. discloses a process and column which strips methanol from a methanol-water mixture, which requires between 50 to 60 percent of the total feed gas stream to flow through the column to effectively regenerate the rich methanol-water stream. The entire 50 to 60 percent of the flow is introduced into the bottom of the column and withdrawn at the top of the column. Hence, the diameter of the column is determined by the 50 to 60 percent of the flow going through the column.

U.S. Pat. No. 3,039,845 to H. Steinrotter et al. disclosed a process of stripping (regenerating) absorbent solutions. This patent covers a splitting arrangement for air so that concentrations of solvent are maintained in the collector and the excess air bypasses directly to the heating section. However, this patent fails to disclose a split column having either a narrower diameter, or shorter split beds for regenerating a volatile liquid from a mixture with a less volatile liquid.

In the present invention, the flow through the column at any time is reduced by approximately 50 percent of that taught by the prior art. Between 25 to 30 percent of the total feed gas stream is introduced at the bottom of the column in the U.S Pat. No. 4,775,395 patent. However, in the present invention although the total bed height may remain the same, the bed is preferably split into two or more sections of equal or unequal height. At the elevation where the beds are split, a dividing means, such as a chimney tray is installed to collect the liquid from the upper bed and redistribute this liquid to the lower bed. Also, a gas outlet is provided between the top of the lower bed and the bottom of the dividing means so that all, or a portion of the gas feed introduced at the bottom is withdrawn. A second gas inlet is provided between the top of the dividing means and the bottom of the top bed to allow introduction of another 20 to 30 percent of the total gas stream. This new gas feed, together with any remaining portion of the gas stream from the lower bed, flows up through the column and leaves from the top of the column.

Therefore, there exists a need in the art for an improved column for regenerating a volatile liquid from a mixture with a less volatile liquid, that may be made at a significantly lower cost, and which produces the same, if not improved results.

SUMMARY OF THE INVENTION

Accordingly, it is a general object of the present invention to provide an improved column for regenerating a higher volatility liquid from its mixture with another liquid of lower volatility. It is a particular object of the present invention to provide an improved column for regenerating a volatile liquid from a mixture with a less volatile liquid, which column has a reduced diameter. It is a further particular object of the present invention to provide an improved column for regenerating a volatile liquid from a mixture with a less volatile liquid, which column splits the feed gas flowing therethrough. It is a more particular object of the present invention to provide an improved column for regenerating a volatile liquid from a mixture with a less volatile liquid, having a split bed through which a feed gas and a gas-water mixture flows. And, it is yet a still further particular object of the present invention to provide an improved column for regenerating a volatile liquid from a mixture with a less volatile liquid, having split beds and feeds whereby the diameter of the column may be reduced, or the column diameter may be the same and packing bed heights may be reduced.

In accordance with one aspect of the invention, there is provided a circular column having a plurality of packing beds with a plurality of feed gas inlets and outlets connected thereto, to split an entering feed gas so that approximately equal portions are fed through each packing bed. An inlet at the top of the column allows a liquid mixture to be introduced to flow down through the split packing beds.

BRIEF DESCRIPTION OF THE DRAWINGS

The object and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

DETAILED DESCRIPTION OF THE PREFERRED EMBODIMENT

The following description is provided to enable any person skilled in the art to make and use the invention and sets forth the best modes contemplated by the inventor of carrying out his invention. Various modification, however, will remain readily apparent to those skilled in the art, since the generic principles of the present invention have been defined herein specifically to provide for an explanation of an improved gas regeneration column.

Columns for regeneration of gases are known. One such column is set forth in U.S. Pat. No. 4,775,395 ("'395"). The disclosure of the '395 patent is incorporated herein, in its entirely, by this reference thereto.

The present invention is directed to a column, a plurality of packing beds and associated plumbing systems, therefor, used to regenerate liquid mixtures. For clarity of understanding, only some of the components of the assembly, including a column and a plurality of beds, with line representations of the gas and liquid mixture feeds are shown on the drawings and described herein.

Figure 1:
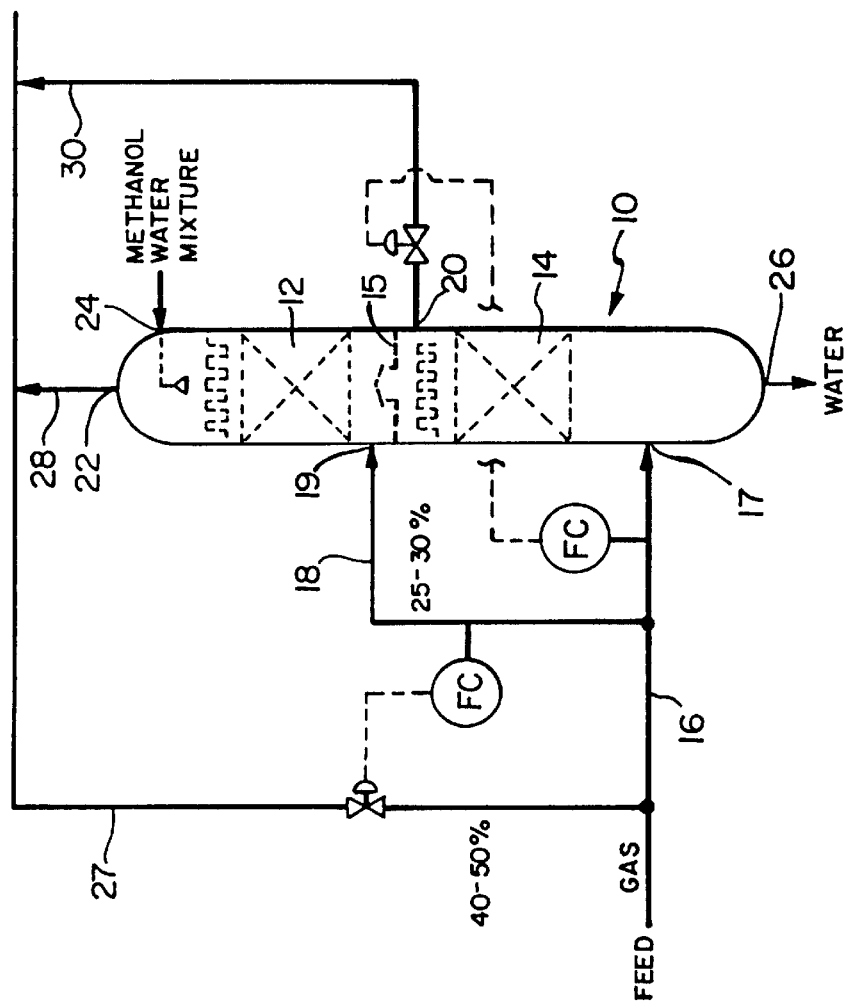
FIG. 1 is a schematic representation of a preferred embodiment of a split bed column of the present invention.

Turning now to FIG. 1 of the drawings, there shown is a column 10, including a first, top or upper packing bed 12 and a second, bottom or lower packing bed 14, formed at the upper and lower ends thereof, with a dividing means 15, such as a chimney tray, therebetween. A first warm gas feed line 16 is connected to an inlet 17 near the bottom of column 10, below the second bed 14, while a second warm gas feed line 18 is connected to a second inlet 19 above the dividing means 15 and below the bottom of the first bed 12. Additionally, the column 10 includes a first gas outlet 20, between the dividing means 15 and the top of the second bed 14, and a second gas outlet 22, at the top of the column. The first and second beds may be of equal or unequal height, and the diameter of column 10 is substantially reduced from the known prior art, such as shown in the '395 patent. This smaller diameter column provides significant savings in costs and materials.

A mixture of water and a liquid, such as methanol, is fed into the column at an upper inlet 24, above the first bed 12, and travels down the column 10, through the beds 12, 14, until the resulting clean water exits from the column 10, via an outlet 26.

The system may include a bypass line 27, which allows the unused portion of the warm gas feed to bypass the column 10. As shown, outlet lines 28 and 30, connected to gas outlets 20 and 22 are connected to the bypass line 27.

Figure 2:
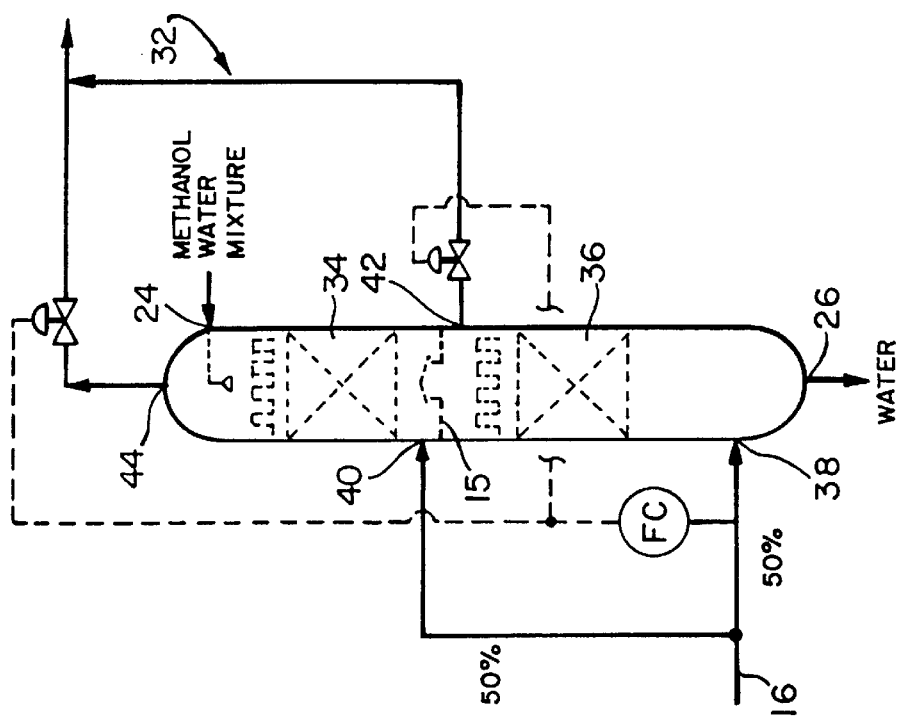
FIG. 2 is a schematic representation of a further, shorter embodiment of the invention.

In the second embodiment of the invention shown in FIG. 2, a shorter column 32 having a larger diameter, which diameter is substantially the same diameter as the prior art column disclosed in the '395 patent, is provided with two beds 34, 36. These two beds 34, 36, because of their larger diameters, are substantially shorter than the beds 12, 14 in column 10, thereby allowing the column 32 to be substantially shorter to again provide significant savings in costs and materials. The beds 34 and 36 may be of equal or unequal heights. In this second embodiment, the bypass line is eliminated, and approximately half or 50 percent of the warm feed gas is fed via line 16 and inlets 38, 40 to the bottom of each bed 34, 36. Two gas outlets 42, 44 are connected to the column 32, one between the top of the second or lower bed 36 and the dividing means 15, and the other at the top of the column 32, in the same manner as the first and second gas outlets 20 and 22 are connected to column 10. Column 32 also includes an inlet 24 for feeding the methanol-water mixture, and an outlet 26 for clean water.

Figure 3:
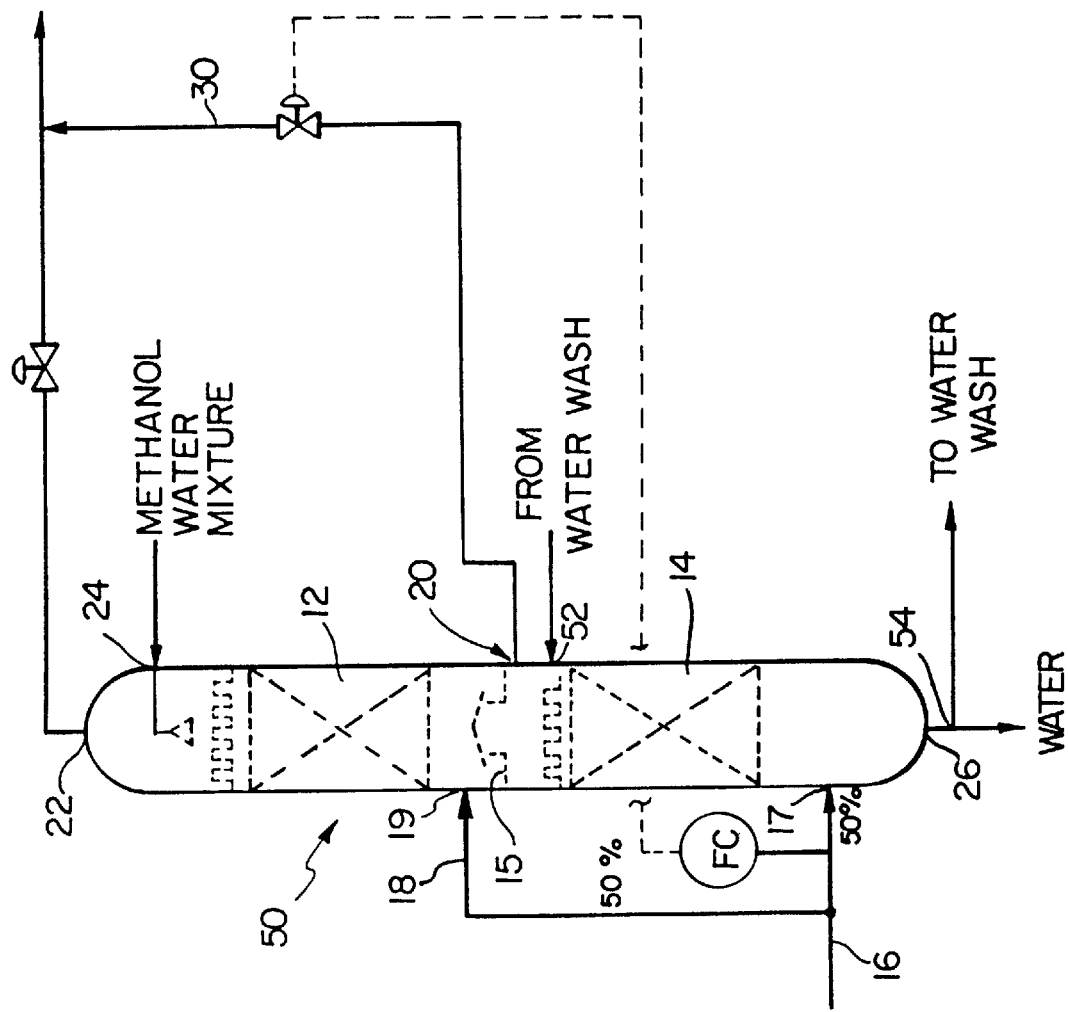
FIG. 3 is a schematic representation of a still further embodiment of the present invention.

Turning now to FIG. 3, there shown is a third embodiment of the invention which illustrates its use for a system employing a water wash to recover methanol from a liquid petroleum gas (LPG). Column 50 of this embodiment is similar in size to the first embodiment shown in FIG. 1, except that the bypass line is eliminated. Column 50 of FIG. 3, however, includes an additional inlet 52 for a wash water return, and an outlet 54 for a wash water supply for the lower bed 14. Therefore, it can be seen that column 50 is equivalent to two separate columns, stacked upon each other, wherein 50% of the warm gas feed enters each bed 12, 14, and the lower bed 14 also receives a separate stream of countercurrent methanol-water wash. However, in this embodiment, the total height of column 50 is substantially less than the height of the two separate columns employed in the prior art.

Those skilled in the art will appreciate that various adaptations and modifications of the just-described preferred embodiments may be configured without departing from the scope and spirit of the invention. Therefore, it is to be understood that, within the scope of the appended claims, the invention may be practiced other than as specifically described herein.

What is claimed is:

1. An apparatus for the separation of a volatile liquid from a mixture with a liquid of lower volatility, comprising, in combination:

a substantially cylindrical column having a top and a bottom, with a second gas outlet at the top, and a water outlet at the bottom;

a first, upper contact zone bed of packing having a top and a bottom held in the substantially cylindrical column;

a second, lower contact zone bed of packing having a top and a bottom held in the substantially cylindrical column, under the first, upper contact zone bed of packing;

a dividing means held in the substantially cylindrical column between the bottom of the first, upper contact zone bed of packing and the top of the second, lower contact zone bed of packing;

a methanol-water liquid inlet connected to the substantially cylindrical column above the top of the first, upper contact zone bed of packing;

a first warm gas inlet connected between a warm gas inlet line and the substantially cylindrical column, below the bottom of the second, lower contact zone bed of packing;

a second warm gas inlet connected between the warm gas inlet line and the substantially cylindrical column, between the bottom of the first, upper contact zone bed of packing and the dividing means;

a first gas outlet connected to the substantially cylindrical column, between the top of the second, lower contact zone bed of packing and the dividing means;

a bypass line connected to the warm gas inlet line to bypass a portion of warm gas fed to the substantially cylindrical column; and a further line connecting the first gas outlet to the bypass line.

2. The apparatus of claim 1 wherein the first, upper contact zone bed of packing and the second, lower contact zone bed of packing are equal in height.

3. The apparatus of claim 1 wherein the first, upper contact zone bed of packing and the second, lower contact zone bed of packing are unequal in height.

4. The apparatus of claim 1 wherein the dividing means is a chimney tray located between the second warm gas inlet and the first gas outlet.

5. An apparatus for the separation of a volatile liquid from a mixture with a liquid of lower volatility, comprising, in combination:

a substantially cylindrical column having a top and a bottom, with a second gas outlet at the top, and a water outlet at the bottom;

a first, upper contact zone bed of packing having a top and a bottom held in the substantially cylindrical column;

a second, lower contact zone bed of packing having a top and a bottom held in the substantially cylindrical column, under the first, upper contact zone bed of packing;

a chimney tray held in the substantially cylindrical column between the bottom of the first, upper contact zone bed of packing and the top of the second, lower contact zone bed of packing;

a methanol-water liquid inlet connected to the substantially cylindrical column above the top of the first, upper contact zone bed of packing;

a first warm gas inlet connected between a warm gas inlet line and the substantially cylindrical column, below the bottom of the second, lower contact zone bed of packing;

a second warm gas inlet connected between the warm gas inlet line and the substantially cylindrical column, between the bottom of the first, upper contact zone bed of packing and the chimney tray;

a first gas outlet connected to the substantially cylindrical column, between the top of the second, lower contact zone bed of packing and the chimney tray;

a bypass line connected to the warm gas inlet line to bypass a portion of warm gas fed to the substantially cylindrical column; and a further line connecting the first gas outlet to the bypass line.

6. An apparatus for the separation of a volatile liquid from a mixture with a liquid of lower volatility, comprising, in combination:

a substantially cylindrical column having a top and a bottom, with a second gas outlet at the top, and a water outlet at the bottom;

a first, upper contact zone bed of packing having a top and a bottom held in the substantially cylindrical column;

a second, lower contact zone bed of packing having a top and a bottom held in the substantially cylindrical column, under the first, upper contact zone bed of packing;

a chimney dividing means held in the substantially cylindrical column between the bottom of the first, upper contact zone bed of packing and the top of the second, lower contact zone bed of packing;

a methanol-water liquid inlet connected to the substantially cylindrical column above the top of the first, upper contact zone bed of packing;

a first warm gas inlet connected between a warm gas inlet line and the substantially cylindrical column, below the bottom of the second, lower contact zone bed of packing;

a second warm gas inlet connected between the warm gas inlet line and the substantially cylindrical column, between the bottom of the first, upper contact zone bed of packing and the chimney dividing means;

a first gas outlet connected to the substantially cylindrical column, between the top of the second, lower contact zone bed of packing and the chimney dividing means; and a wash water return connected to the substantially cylindrical column, between the dividing means and the top of the second, lower contact zone bed of packing, and a wash water supply outlet connected to the water outlet.

7. An apparatus for the separation of a volatile liquid from a mixture with a liquid of a lower volatility, comprising, in combination:

a substantially cylindrical column having a top and a bottom, with a second gas outlet at the top, and a water outlet at the bottom;

a first, upper contact zone bed of packing having a top and a bottom held in the substantially cylindrical column;

a second, lower contact zone bed of packing having a top and a bottom held in the substantially cylindrical column, under the first, upper contact zone bed of packing;

a dividing means held in the substantially cylindrical column between the bottom of the first, upper contact zone bed of packing and the top of the second, lower contact zone bed of packing;

a methanol-water liquid inlet connected to the substantially cylindrical column above the top of the first, upper contact zone bed of packing;

a first warm gas inlet connected between a warm gas inlet line and the substantially cylindrical column, below the bottom of the second, lower contact zone bed of packing;

a second warm gas inlet connected between a warm gas inlet line and the substantially cylindrical column, below the bottom of the first, upper contact zone bed of packing and the dividing means;

a first gas outlet connected to the substantially cylindrical column, between the top of the second, lower contact zone bed of packing and the dividing means; and a wash water return connected to the substantially cylindrical column, between the dividing means and the top of the second, lower contact zone bed of packing and a wash water supply outlet connected to the water outlet.

* * * * *